United States Patent [19]

Groger et al.

[11] Patent Number: 5,514,337
[45] Date of Patent: May 7, 1996

[54] CHEMICAL SENSOR USING EDDY CURRENT OR RESONANT ELECTROMAGNETIC CIRCUIT DETECTION

[75] Inventors: Howard P. Groger, Gainesville, Fla.; Russell J. Churchill, Radford, Va.; James Kelsch, Gainesville, Fla.

[73] Assignee: American Research Corporation of Virginia, Radford, Va.

[21] Appl. No.: 179,679

[22] Filed: Jan. 11, 1994

[51] Int. Cl.$^6$ .......................... G01N 27/02; G01N 27/06; G01N 27/12
[52] U.S. Cl. ................. 422/82.08; 422/108; 324/207.15; 324/607; 324/658; 324/654
[58] Field of Search ................................. 422/82.02, 107; 436/149, 150, 151; 324/207.15, 607, 658, 654

[56] References Cited

U.S. PATENT DOCUMENTS

| | | |
|---|---|---|
| 4,059,795 | 11/1977 | Modwinkin . |
| 4,225,410 | 9/1980 | Pace . |
| 4,312,228 | 1/1982 | Wohltzen .................................. 73/597 |
| 4,472,356 | 9/1959 | Kolesar, Jr. . |
| 4,553,094 | 11/1985 | Gehrke . |
| 4,822,566 | 4/1989 | Newman . |
| 4,859,940 | 8/1989 | Hummert et al. . |
| 4,871,427 | 10/1989 | Kolesar, Jr. . |
| 4,906,440 | 3/1990 | Kolesar, Jr. ................................ 422/98 |
| 4,959,778 | 9/1990 | Champonnois et al. . |
| 5,003,262 | 3/1991 | Egner . |
| 5,017,869 | 5/1991 | Oliver . |
| 5,028,394 | 7/1991 | Lowell, Jr. et al. . |
| 5,045,285 | 9/1991 | Kolesar, Jr. ................................ 422/98 |
| 5,055,784 | 10/1991 | Jaeger et al. ............................ 324/233 |
| 5,061,364 | 10/1991 | Metala et al. . |
| 5,071,770 | 12/1991 | Kolesar, Jr. . |
| 5,076,094 | 12/1991 | Frye et al. . |
| 5,108,576 | 4/1992 | Malmros et al. ........................ 204/403 |
| 5,120,505 | 6/1992 | Lowell, Jr. et al. ....................... 422/58 |
| 5,146,164 | 9/1992 | Masui et al. ............................. 324/233 |
| 5,232,667 | 8/1993 | Hieb et al. ............................ 422/82.04 |
| 5,235,267 | 8/1993 | Schoneberg et al. ................... 324/71.5 |

FOREIGN PATENT DOCUMENTS 0685971  6/1976  U.S.S.R. .

OTHER PUBLICATIONS

Krutovertser et al "Polymer film–based sensors for ammonia detection".
Ashraf, M. S., and Borah, D. K., (1992), Modeling Pollutant Transport in Runoff and Sediment, Transactions of the ASAE, vol. 35, No. 6, pp. 1789–1797.
Baughman, R. H., (1991), Conducting Polymers in REdox Devices and Intelligent Materials Sytesm, Makromol. Chem. Makromol. Symp., vol. 51, pp. 193–215.
Blake Coleman, B. C., Cossar, J. D., Clarke, D. J. and Ramsay, C. (1990), Oscillomet Instrumentation for the No–Invasive Detection of Low–Level Microbial Activity. Part 1, Apparatus, Biosensors and Bioelectronics, vol. 5, pp. 235–258.

(List continued on next page.)

*Primary Examiner*—Timothy M. McMahon
*Assistant Examiner*—N. Bhat
*Attorney, Agent, or Firm*—James Creighton Wray

[57] ABSTRACT

An instrument is applied to the measurement of chemical species and concentration through the use of a chemically-sensitive coating on the eddy current coil or in the vicinity of the eddy current coil which produces a change in impedance of the probe through induced eddy currents in the coating. An eddy current or resonance circuit chemical detector is a non-contact sensor for measuring chemical species identity and concentration. The chemical detector is resilient and does not require reference electrodes. The chemical sensor is selective as a result of data available on the change in vector impedance of the probe, the change in resonant frequency of the tuned circuit, and the availability of data to construct a vector response from multiple probes having differing chemistries. The probe is used in extreme temperatures.

20 Claims, 5 Drawing Sheets

OTHER PUBLICATIONS

Churchill, R. J. and Groger, H. P., (1988), Electromagnetic Detection of Stress and Crack Propagation in Critical Aircraft Components, U.S. Department of the Navy, SBIR Final Technical Report, Contract N000019–85–C–0361.

Churchill, R. J., Groger, H. P. and Lo, K. P., (1992), Self–Assembled Thin Film Sensors for Aquaculture Process Control, U.S. Department of Agriculture, SBIR Phase I Report, Grant No. 92-33610–7218.

Giuliani, J. F. and Keller, T. M. (1989), Phthalonitrile Conductive Polymer Chemica Vapor Sensors, Sensors and Materials, vol. 1, pp. 247–253.

Krutovertsev, S. A., Sorokin, S. I., Zorin, A. V., Letuchy, Y. A. and Antonova, O. Y. on the Ionically Conductive Polymer Poly (dimenthyldiallylammonium chloride).

Thackeray, J. W., White, H. S. and Wrighton, M. S. (1985), Poly(3–methylthiophene)–Coaed Electrodes: Optical and Eelctrical Properties as a Function of Redox Potential and Amplification of Electrical and Chemical Signals Using Poly(3–methylthiophene)–based Microelectrochemical Transistors, J. Phys. Chem., vol. 89, pp. 5133–5140.

Heeger, A. J. (1991), Conducting Polymers: The Route from Fundamental Science to Technology, Science and Applications of Conducting Polymers, Edited by W. Slaneck, lark and E. Samelsen, Adam Hilger/IOP Publishing Ltd. pp. 1–12.

Whittington et al., An On–Line Wear Debris Monitor, Measurement Science and Technology vol. 3 (1990) pp. 656–661.

Blake–Coleman et al., Biosensors and Bioelectronics, vol. 5, (1990), pp. 235–258.

Takemae et al., IEEE Transaction on Biomedical Engineering, vol. 37 (1990), pp. 53–59.

Teasdale and Wallace, Analyst vol. 118 (1993 , pp. 329–334.

Slater et al., Analyst, vol. 118 (1993), pp. 379–384.

AOAC., (1990), Official Methods of Analysis of the Association of Official Analytical Chemists, Arlington, VA.

Miller, G. L., Robinson, D. A. H. and Wiley, J. D., (1976), Contactless Measurement of Semiconductor Conductivity by Radio Frequency–Free–Carrier Power Absorption, Review of Scientific Instruments, vol. 47, No. 7, pp. 799–805.

Tieman, R. S., Heineman, W. R., Johnson J. and Sequin, R. (1992), Oxygen Sensors Base.

CHEMICAL SENSOR USING EDDY CURRENT OR RESONANT ELECTROMAGNETIC CIRCUIT DETECTION

BACKGROUND OF THE INVENTION

The present invention applies to chemical sensors, resonant sensors and eddy current instruments.

Recent efforts to provide a cleaner environment through reduction of point source and non point source pollution require the availability of chemical sensors to measure the presence and concentration of pollutants, including industrial gaseous emissions such as nitrous oxide, sulfur dioxide, hydrocarbons and liquid emissions such as nitrates, phosphates, ammonia-saturated liquids, chlorinated hydrocarbons and toxic materials.

Commercially available sensors for gaseous and liquid pollutants include ion selective electrodes (ISE's) and semiconductor potentiometric sensors with accuracy affected by numerous interfering agents. Furthermore, ISE's require the use of a reference electrode, may be fragile, respond slowly, are subject to fouling and require frequent calibration.

A resonant eddy-current instrument has been demonstrated to measure small changes in the conductivity of saline solutions caused by the growth of micro-organisms in a saline-based buffer. The change in resonance frequency with solution conductivity was found to be approximately 280 Hz per micro Siemens per centimeter indicating the range of instrument responses expected to five orders of magnitude changes in polymer conductivity.

Previous work in conductive polymer chemical sensors has relied upon the use of electrodes and electrode arrays for signal excitation and detection. Feasibility has been discussed for joining conductive polymer to a resonant metallic glass substrate for excitation by a radio-frequency electromagnetic wave. The use of a phthalonitrile conductive polymer resin as a reversible sensor for ammonia gas has been demonstrated. The intrinsic room temperature electrical conductivity of the phthalonitrile could be varied from 2 Siemens per meter to 20,000 Siemens per meter through suitable choice of the pyrolyzation temperature. The use of a polyaniline film based sensor in the detection of ammonia providing a 1585% change in conductivity upon exposure to ammonia gas has been shown.

Needs exist for chemical sensors which are precise, rugged, dependable, inexpensive and reliable.

SUMMARY OF THE INVENTION

This invention provides a family of chemical sensors that are built based upon the interaction of an excitation electronic or electromagnetic signal with a chemically sensitive thin film or thick film, allowing precise measurement of changes in the conductivity, dielectric constant or magnetic properties of the chemically sensitive film originating from interaction with the chemical under test.

The invention provides chemical sensors based upon either eddy current detectors or a resonant resistance-inductance-capacitance circuits in combination with films. The films are absorbent films for specific chemicals or films which plate or react in specific ways with specific chemicals. An example uses 10 probes with 10 conductive polymers. Each has a different composition; each has a different response. A resultant response has a vector which precisely identifies the chemical. Running through a number of frequencies identifies a chemical. The films may be conducting polymers, ionic conducting polymers, ceramic films, ferroelectric films or films with alterable magnetic properties. The films are exposed to a chemical analyte. The direct contact of the film with the chemical analyte alters the properties of the film. The altered properties of distinct films are detected as changes in impedance of eddy current probes in the vicinity of the films or in the changes of the resonance frequency of a tuned circuit in the vicinity of the film.

Chemical sensors of the present invention are based upon either a resonant resistance-inductance-capacitance (RLC) circuit, microwave or millimeterwave circuit or an eddy current detector used in combination with a probe, which has a conducting polymer, an ionic conducting polymer or ceramic film, a ferroelectric film, a film with alterable magnetic properties, a film comprised of alternating layers or a composite material. The conducting polymer film, ceramic film, ferroelectric film, magnetic, layered or composite film is exposed to the chemical analyte, thereby altering the properties of the film. The altered properties are detected as a change in the impedance of an eddy current probe in the vicinity of the film, change in the mutual inductance of wound coils in the vicinity of the film, change in the circuit parameters of a microwave, millimeterwave circuit in the vicinity of the film or in the change of the resonance frequency of an adjustable tuned circuit in the vicinity of the film.

In particular, the eddy current probe may be used in proximity to a conducting polymer film of polypyrrole, polythiophene or polyaniline which is exposed to the chemical of interest. The change in conductivity resulting from ionic exchange of the dopant of the conductive polymer is detected as a change in either the impedance of the eddy current probe or as a change in the resonance frequency of a resonant circuit in the vicinity of the conducting polymer. When polypyrrole is used as the sensor material of interest, counterions such as chlorine, bromine, sulphate or chromate may be incorporated into the thin film.

An eddy current system can be used as the basis for a chemical sensor when placed in the proximity of a conducting polymer or other chemically reactive film to provide direct readout of film conductivity for samples having conductivities as low as 1 Siemen per meter or less and as thin as 1 mm or less. Multiple films may be arranged in the gap of a ferrite core inductor, providing a measure of the total conductivity of each layer. The eddy current probe can be driven in a circuit designed to detect small changes in resonance frequency and phase using direct digital synthesis to provide the starting signal. The probe is used as an inductor in an LC oscillator circuit. A digital microprocessor detects the resonant frequency and adjusts the driving frequency to compensate for inductance changes caused by eddy current interaction with the sensor.

The chemically sensitive film used to provide the impedance change necessary for chemical recognition may be a conductive polymer. The present invention uses conductive polymers and ceramic-polymer (ceramer) composite materials as sensors for an eddy current chemical analyzer. Conducting polymers are sensitive to oxidation-reduction processes in the sensor environment with conductivity changes of five orders of magnitude accompanying exposure to oxidizing or reducing conditions. Several families of conducting polymers are available with high electron affinity or low ionization potential such that they can be readily doped with electron donors or acceptors to form charge-transfer complexes.

At present, the most widely used conducting polymers are based on polypyrrole, polythiophene and polyaniline. The conducting polymers are prepared by chemical, electrochemical or pyrolization techniques. In the chemical and electrochemical methods, electron transfer reactions result in the conductivity of the sample. Oxidative doping of a conductive polymer produces a positive charge that is delocalized over several polymer units. To maintain charge neutrality, it is necessary to incorporate anionic species as counterionic dopants.

The molecular recognition characteristics exhibited by conducting polymers is directly related to the counterionic dopants incorporated in the thin film. A range of counterionic dopants is incorporated in polypyrroles. Surfaces capable of recognizing metallic components have been prepared by addition of dithiocarbamates or ethylenediaminetetraacetic acid. Surfactants and colloidal gold have been incorporated in polypyrroles to function as molecular carriers for improved sensor specificity. Additional capabilities in molecular recognition are attained through use of the inherent anion-exchange capacity of the polymer due to delocalized positive charges distributed along the polymer structure. The ion-exchange selectivity series of polypyrrole is determined by the counter ion incorporated during synthesis. Functional groups can be added to the base monomer to improve sensor specificity. The creating of other sensor films includes the production of copolymers or interpenetrating layer structures.

Metal oxide semiconductors such as zinc oxide, tin oxide and a range of rare earth metal oxides can be used for gas sensing when placed in proximity to an eddy current instrument or resonant circuit instrument. Conductive materials such as ruthenium oxide and yttrium barium copper oxide can be used with the low frequency eddy current probe directly, whereas insulating materials can be used with a high frequency (greater than 50 MHz) eddy current instrument or with an insulator incorporated in the inductor or resistor section of the RLC instrument.

In cases where the chemically-sensitive film is an electrical insulator, an RLC circuit or microwave circuit is preferred to the eddy current method. In the RLC circuit, the signal may be generated by direct digital synthesis, look-up table sampled waveform generator, relaxation oscillators, marginally stable recursive filter oscillators or crystal oscillators employed in a phase locked loop.

Electrochemical sensors are well known but require a reference electrode for their operation. Nuclear magnetic resonance (NMR) and electron spin resonance (ESR) are chemical methods of analysis that use alternating currents for excitation. A resonance instrument employing a marginal oscillator within a phase-locked loop measures small changes in the magnetic circuit of a wear-debris monitor, but does not describe the use of chemical-specific coatings for chemical species identification or quantification. An oscillometric instrument non-invasively detects microbial activity. The instrument provides non-contact measurement of bacterial concentration and does not require an electrode, but the instrument can only measure conductivity and does not describe the use of multiple probes to provide chemical specificity. A non-contact method of measuring blood flow in human extremities is highly accurate but does not provide the use of chemical-specific coatings for chemical analysis. Multiple conducting polymers have been used to produce a chemical sensors. In particular, polypyrole is shown to provide a range of conductivities in the presence of a wide range of analytes. Incorporation of counterionic materials into the conducting polymer alter the sensitivity of the material to specific chemical species. A technique has been described to reduce data from multiple conducting polymers to provide a chemical-specific response.

Jaeger and Groger have described in U.S. Pat. No. 5,055,784 an all digital eddy current instrument to detect the change in impedance of a coil or other eddy current probe through measuring the current through the coil by measuring the voltage drop across a resistor in series with the coil, and through measuring the phase change of the driving signal after the signal passes probe.

An eddy current instrument has been described based on detuning of a resonant circuit caused by the impressed eddy current on a probe in the vicinity of the material under test. An eddy current instrument has been described employing resonance detection from two sensor coils.

An eddy current chemical sensor includes an eddy current measuring probe having an electromagnetic coil, and a conductive coating containing a chemically sensitive material. The eddy current measuring system can be similar to that described in U.S. Pat. No. 5,055,784.

In one embodiment, an electromagnetic chemical sensor has an adjustable tuned resistance, inductance, capacitance circuit, and a circuit containing one or more direct digital synthesizer circuits and one or more digital signal processor circuits in proximity to a chemically sensitive film. Another example of a suitable chemically sensitive film is a conducting polymer such as polypyrrole containing one or more dopants to provide sensitivity to the material of interest.

One embodiment of the chemically sensitive film is a rare earth perovskite oxide, and may or may not be heated.

In a preferred electromagnetic chemical sensor, a microstrip line, coplanar line, coupled microstrip line or other microwave circuit transmission line is placed in the vicinity of the chemically sensitive film. The chemically sensitive film is a conducting polymer such as polypyrrole containing one or more dopants to provide sensitivity to the material of interest.

One example of the present invention provides a chemical sensor consisting of (a) a chemically sensitive film which exhibits altered electrical conductivity, dielectric constant or magnetic permeability in response to a change in its chemical environment, (b) an electromagnetic transducer comprising an eddy current resonant electrical circuit, microwave transmission line or microwave resonator in proximity to the chemically sensitive film, and (c) electronic circuitry to excite the transducer and detect small changes in electrical impedance, resonance frequency of inductive coupling of the circuit elements.

These and further and other objects and features of the invention are apparent in the disclosure, which includes the above and ongoing written specification, with the claims and the drawings.

DETAILED DESCRIPTION OF THE DRAWINGS

The present invention uses eddy current, resonant circuit and microwave transmission line probes in measuring chemical concentrations when driven by appropriate electronic or microwave circuits.

Physically, conductive polymers and composites produced from conductive polymers used in the eddy current chemical sensor may be classified as non-ferromagnetic anisotropic solids containing conductive and dielectric elements, which when excited by steady-state, sinusoidally time-varying signals behave according to Maxwell's equations:

$$\nabla \times \overline{E} = -j\omega\mu_o \overline{H} \quad (1)$$

$$\nabla \times \overline{H} = j\omega\epsilon\overline{E} + \sigma\overline{E} \quad (2)$$

where the variables, $\overline{E}$ and $\overline{H}$, are phasor vectors representing the electric and magnetic field strengths, respectively, $\mu_o$ is the material magnetic permeability assumed to be equal to the free space magnetic permeability, $\epsilon$ and $\sigma$ are the permittivity and conductivity tensors, respectively, of the anisotropic composite material, and $\omega$ is the angular frequency ($2\pi f$) of the excitation source. The permittivity and conductivity tensor terms in Equation 2 are functions of the excitation frequency because of dielectric polarization phenomena associated with insulating portions of the sensor head. The description of the interaction of eddy current signals and anisotropic sensor materials having conductive and dielectric components will include contributions from each component.

Figure 1:
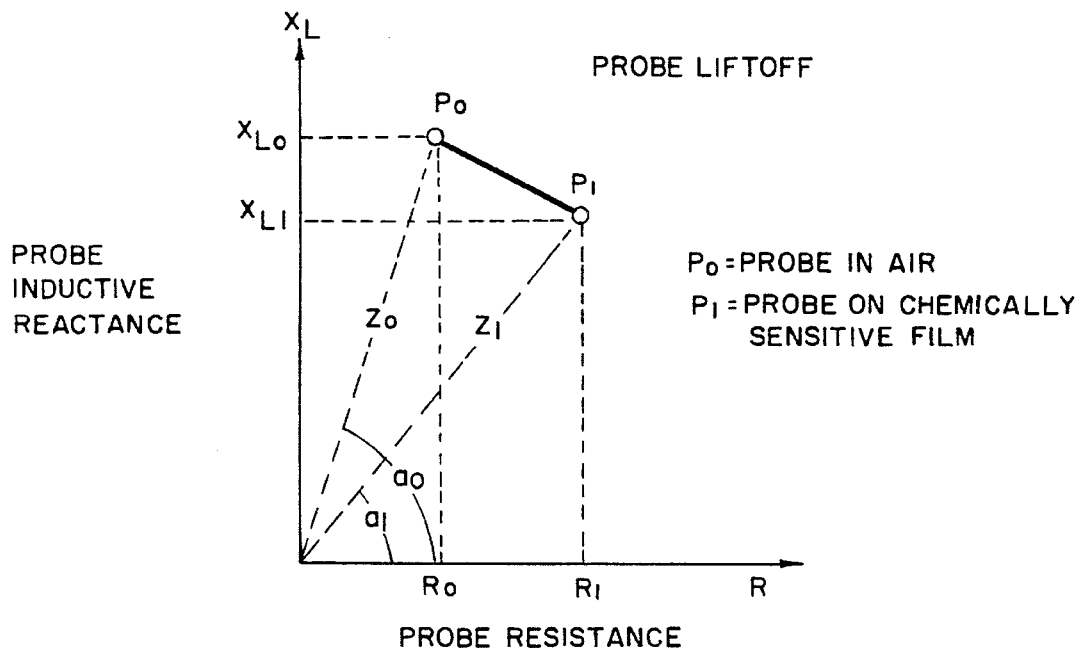
FIG. 1 is a schematic illustration showing the response of an eddy current sensor to changes in the impedance of a chemically sensitive film in the proximity of the probe.

In regions of the composite material where $\sigma/\omega\epsilon \gg 1$, the conduction current exceeds the displacement current. The key factor governing the propagation of eddy currents in such regions is the propagation constant, $\gamma$, given by:

$$\gamma = \alpha + j\beta = (j\omega\mu_o(\sigma + j\omega\epsilon))^{1/2} \quad (3)$$

where $\alpha$ and $\beta$ are the attenuation and phase contents, respectively. For good conductors, $\delta = \frac{1}{2}\alpha$, where $\delta$ is the characteristic skin depth of the conductor given by $\delta = 660.44/\sqrt{\mu\sigma}$. In order to describe the macroscopic eddy current characteristics of the anisotropic sensor material, it is necessary to define the complex permittivity tensor. In general, a test probe (inductor coil) may be characterized by its resistance, R, in ohms and by its inductive reactance $X_L = 2\pi f L$, (where $X_L$ is in ohms, f is the excitation frequency in Hz and L is the probe self inductance in Henrys). The reactance, $X_L$, is plotted as the ordinate and the resistance, R, is plotted as the abscissa in the impedance plane where the probe impedance, Z, in ohms is given by $(R^2 + X_L^2)^{1/2}$. With no chemically sensitive film present, the rest probe has an impedance with coordinates $X_{LO}$ and $R_0$ as shown in FIG. 1 as point $P_0$, or the so-called air-point. When the probe coil is placed in the vicinity of the sensor material, the impedance of the coil is modified to $X_L$ and R, as shown by the new operating point, $P_1$, in FIG. 1. The magnitude and direction of the displacement of the apparent impedance from P0 to $P_1$ are functions of the instrumentation used to monitor the change. For the sensor material, electrical conductivity, dimensions, magnetic permeability and materials defects must be considered, while the instrumentation features of interest include the frequency of the alternating current excitation field, the geometry of the test coil and the distance from the test coil to the sensor material, called the "lift-off". Changes in excitation frequency move the material impedance points along the conductivity locus in a nonlinear fashion. At low frequencies and low sensor conductivities, the separation angle, $\Theta$, is quite small, making it difficult to obtain suppression of the lift-off signal. For higher frequencies, the separation angle, $\Theta$, increases and facilitates suppression of the unwanted lift-off signal. Thus appropriate frequency selection can enhance the use of eddy current technology in obtaining information on sensor electrical properties, thereby improving instrument performance.

Figure 2:
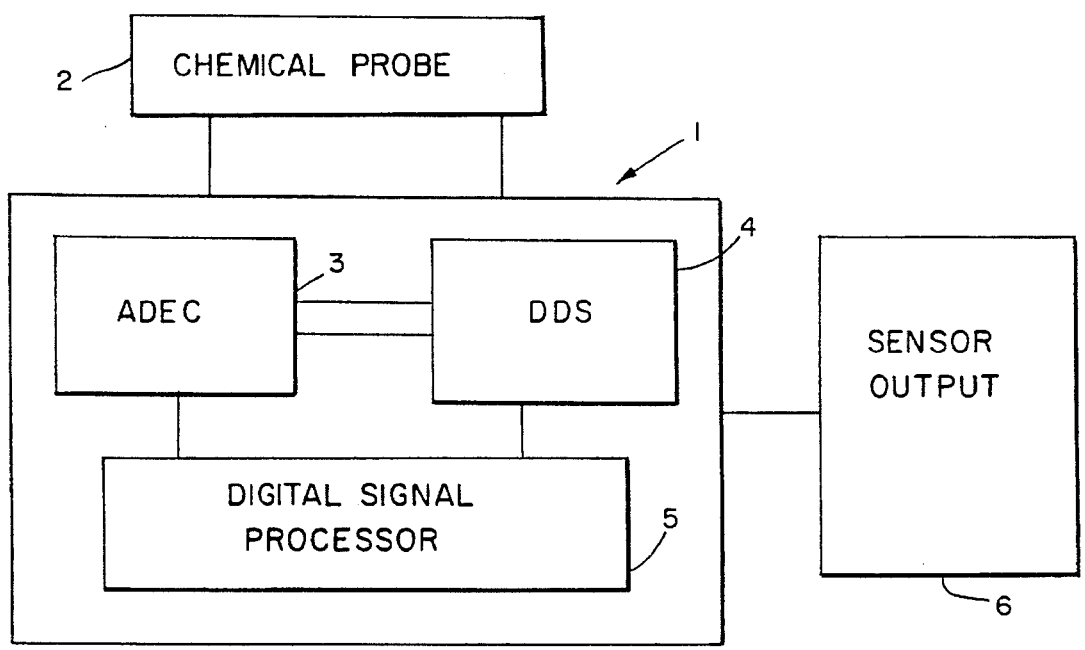
FIG. 2 is a schematic illustration of an eddy current instrument which is used in the present invention as a chemical sensor.

The eddy current instrument 1 shown schematically in FIG. 2 has a chemical probe 2, an all-digital eddy current measurement (ADEC) system 3, a direct digital synthesizer (DDS) 4, a digital signal processor and associated electronics 5, and a sensor display output 6. The use of digital signal processing allows instrument self-calibration, signal averaging and data acquisition.

Figure 4:
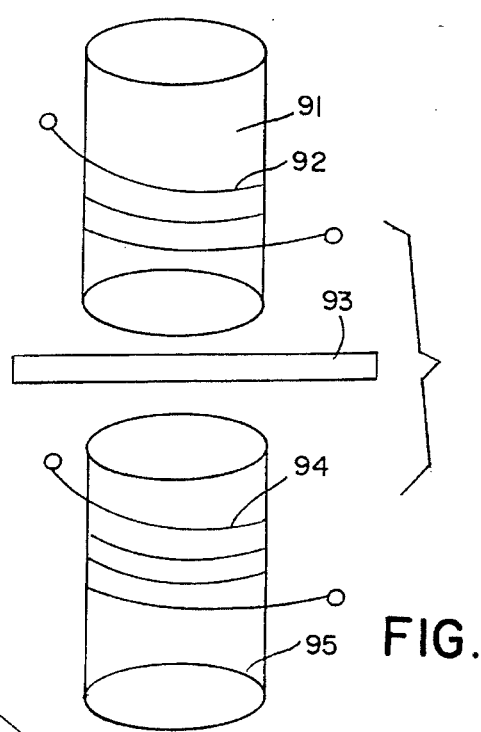
FIG. 4 shows a double inductor eddy current probe.
Figure 5:
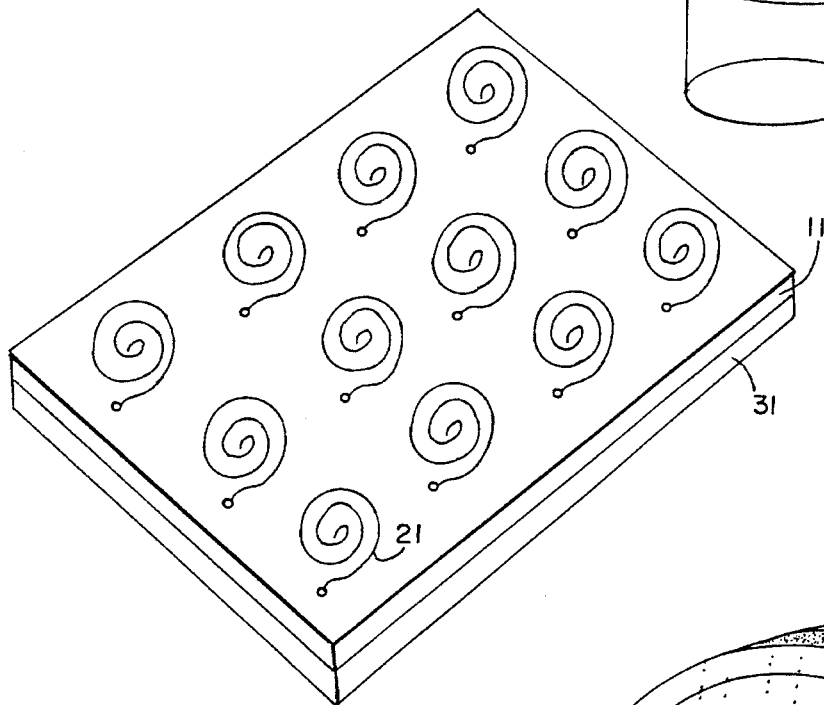
FIG. 5 shows the configuration of the eddy current probe over the chemically-sensitive conductive polymer.
Figure 6:
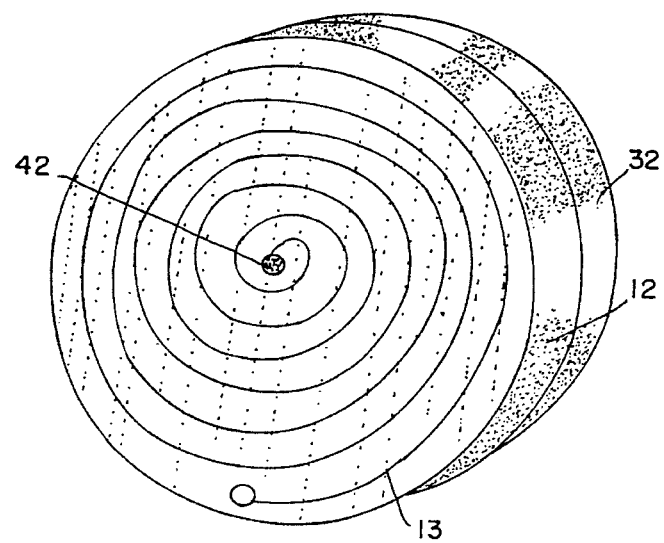
FIG. 6 shows a spiral eddy current probe over a chemically-sensitive conductive polymer.

A prior art eddy current probe from FIG. 2 of U.S. Pat. No. 5,055,784 is shown schematically in FIG. 3. The probe includes a probe housing 14, a coil L, and a core 16. In the present invention, the material under test is a chemically sensitive material. FIG. 4 shows a double inductor probe where the chemically sensitive film 93 is positioned between coil 92 wound around ferrite core 91 and coil 94 wrapped around ferrite core 95. FIGS. 5 and 6 describe an array of eddy current probes and a single eddy current probe respectively.

In FIG. 5, the inductive eddy current probes 21 are formed by chemical deposition or chemically etching a copper clad printed circuit board substrate 11. The chemically sensitive material 31, which may be a conductive polymer film formed from polypyrrole, may be deposited directly onto the inductor array, as shown in FIG. 5, or may be separated from the array by spacers. The chemically sensitive material may be formed as a spiral and joined to the substrate using an appropriate adhesive. Numerous other probe geometries are available for use in low frequency, radio frequency and microwave applications. Lumped inductors may be formed in spiral, loop and strip geometries. The chemically sensitive film may also be affixed to a dielectric substrate to form a microstrip ring resonator, a rectangular strip resonator or a finline resonator. Additional microwave or millimeter wave resonator configurations may also be used in the formation of the chemically sensitive probe.

FIG. 6 shows a spiral-wound inductor eddy current probe 13, with a thick film ferrite core 42 deposited on a printed circuit board substrate or etched on a printed circuit board substrate 12. The chemically sensitive film 32 may be deposited directly onto the substrate or fabricated as a free standing film separated from the substrate by spacers.

The electronic instrument for measuring the eddy current or microwave signal from the probe can be similar to that described by Jaeger and Groger in U.S. Pat. No. 5,055,784.

Figure 7:
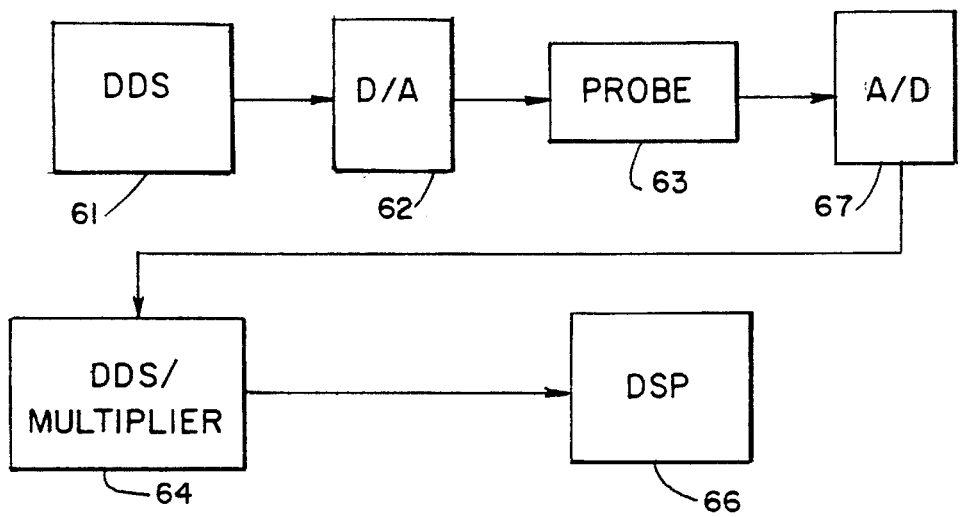
FIG. 7 is a schematic illustration showing the configuration of electronic circuitry to detect changes in signal amplitude and phase accompanying changes in the sample conductivity, dielectric constant or magnetic properties.
Figure 8:
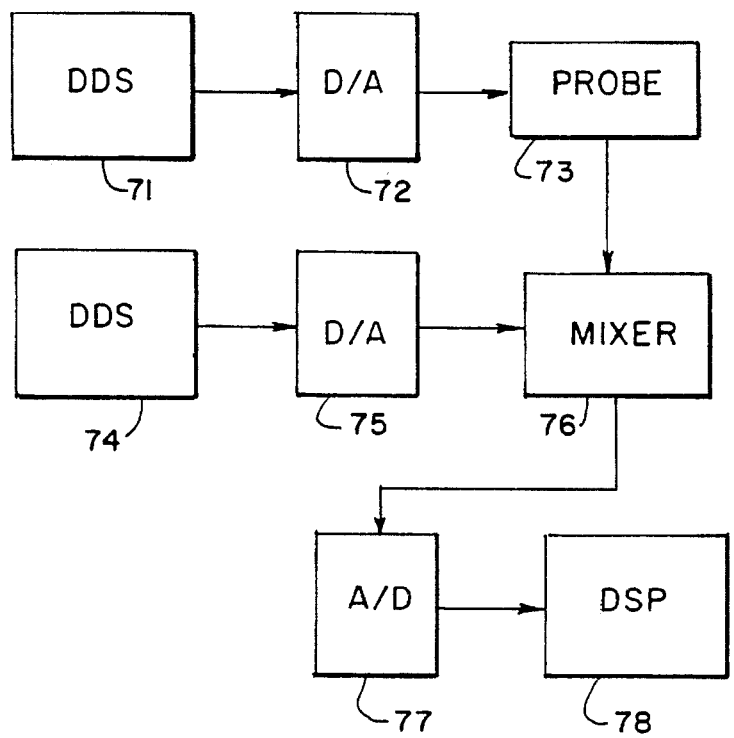
FIG. 8 shows the use of an analog mixer to provide a downconverted signal prior to signal analysis.

Particularly favorable configurations of the instrument, shown schematically in FIGS. 7 and 8, use direct digital synthesizer (DDS) circuits such as the HSP-45116 (Harris Semiconductor DSP Products) to provide an input waveforms, digital-to-analog converters, flash analog-to-digital converters and digital signal processors (DSP) such as the TMS320C5x (Texas Instruments).

A most favorable configuration shown in FIG. 7 uses a Harris HSP 50016 digital down converter as the DDS/Multiplier, 64. The digital down converter operates by generating a complex sinusoid having both sine and cosine components. The data input to the digital down converter is multiplexed to form two channels. One channel is multiplied by the cosine form of the complex sinusoid and is called the "i" channel. The other is multiplied by the sine and is called the "q" channel. Both channels then pass through a high decimation filter and a low pass digital filter.

One configuration shown in FIG. 7 uses one DDS circuit 61 and digital-to-analog converter 62 to generate a sinewave waveform to be fed via probe 63 to the device under test. The device under test may be an inductor, capacitor or microwave line in proximity to the chemically sensitive film. Microwave frequency generation may be accomplished using a DDS in conjunction with digital-to-analog converter and an upconverter such as the Phillips UMA1014T. An analog-to-digital converter 67 is used to convert the signal from the probe and the device under test to a digital signal, which is then brought to a second DDS/Multiplier 64 and multiplied by a second sinewave generated by the second DDS 64. The output of the second DDS contains data that represents the phase delay and amplitude change caused by the device under test and is processed by the DSP, 66.

When the Harris HSP 50016 digital down converter is used as the DDS/Multiplier, 64, the phase difference imposed by the probe is calculated by averaging the ratio of the amplitude of the "q" channel divided by the amplitude of the "i" channel. The signal is then conditioned using the digital signal processor. When the data is obtained using the input to the probe and the phase shifted output from the probe, the phase difference is calculated from the inner product formed by multiplying corresponding samples from the input and output sinewaves and summing over the total number of samples in a given time interval.

Alternatively, in the circuit as shown in FIG. 8, first and second DDS's 71 and 74 may be operated with a slight offset frequency, say 25 Hertz. The output of the first DDS 71 is converted to an analog signal by the digital-to-analog converter 72, brought to the device under test by probe 73. The signal from the probe 73 and the device under test is multiplied by the signal from the second DDS 74 and converter 75, using a nonlinear analog mixer 76 or analog-to-digital converter and digital mixer. The output is converted to a digital signal in A/D converter 77 and processed in the DSP 78, as shown schematically in FIG. 8.

Figure 13:
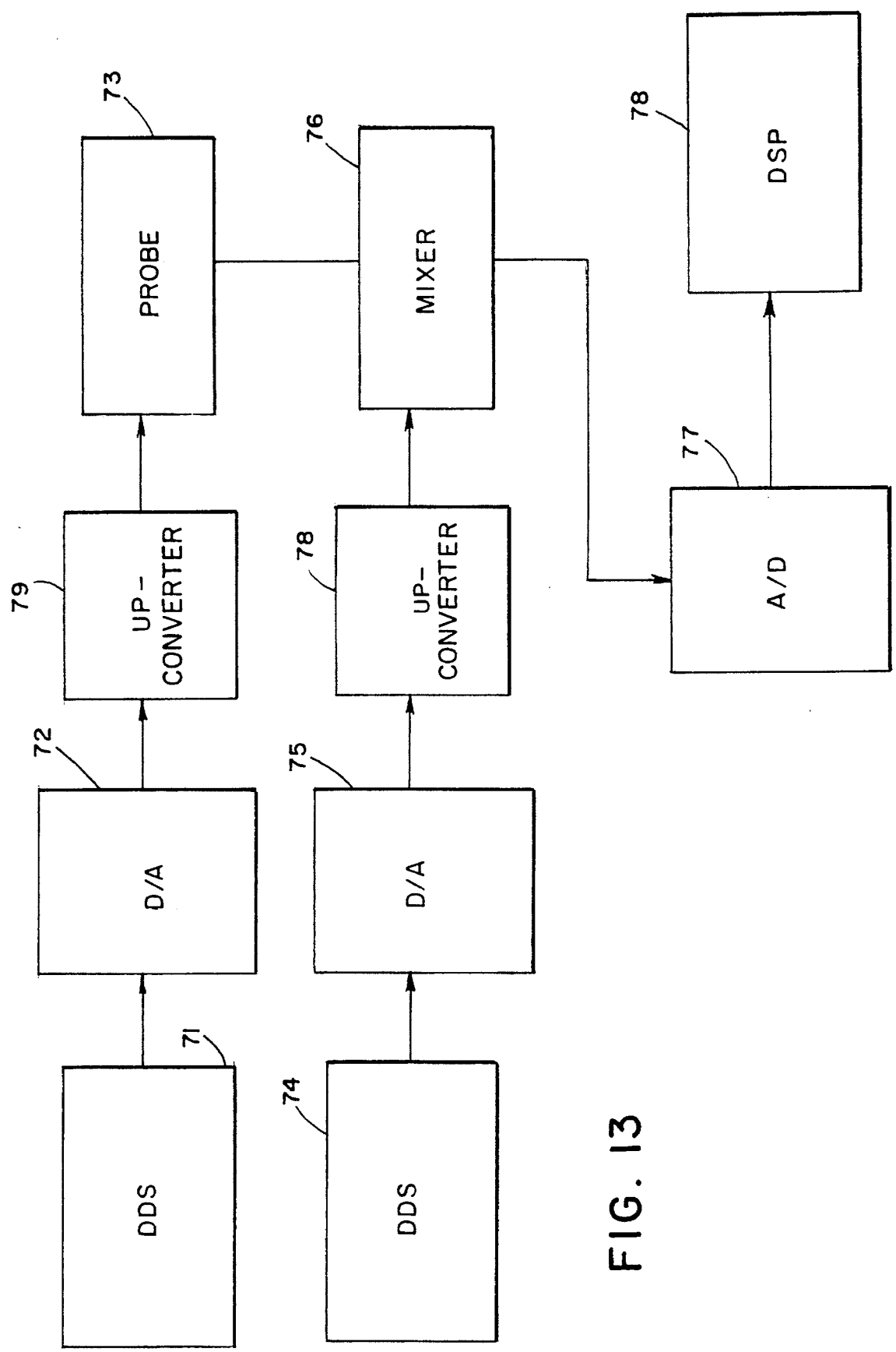
FIG. 13 shows the circuit of FIG. 8 having a first upconverter and a second upconverter.

The microwave instrument, as shown in FIG. 13, is identical to the eddy current instrument in FIG. 8, except an upconverter 79 is inserted between the digital-to-analog converter 72 and the probe 73, and a second upconverter 78 is inserted between the second digital-to-analog converter 75 and the mixer 76.

Figure 9:
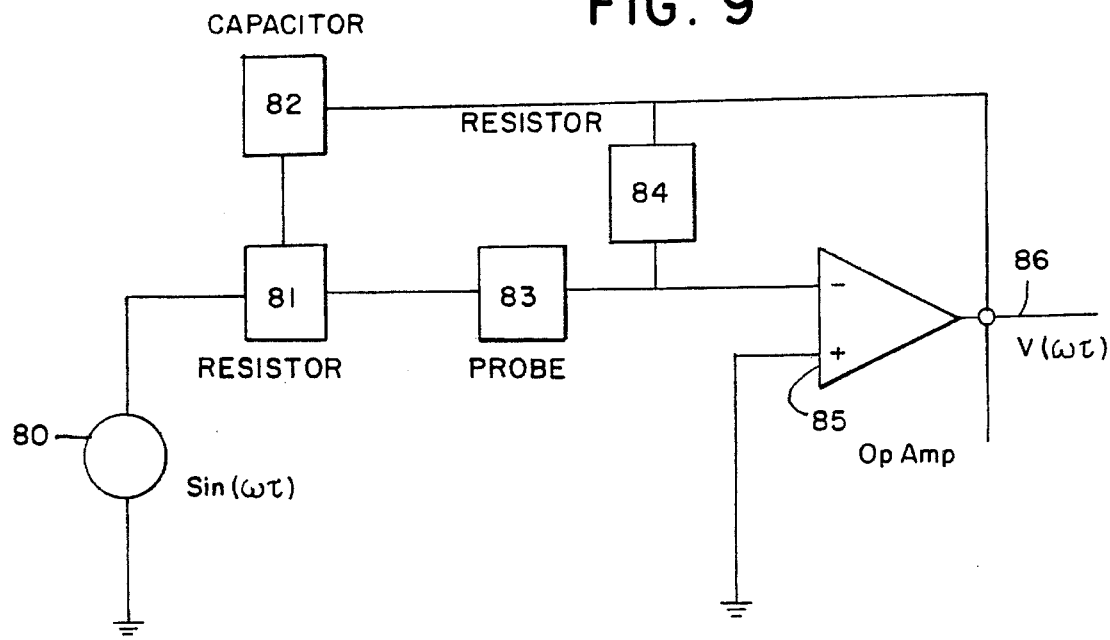
FIG. 9 is a schematic illustration of a circuit element used as a chemical sensor.

In FIG. 9 a sensor circuit is schematically shown with a sinewave generator 80, a resistor 81, a capacitor 82, the probe 83 and a second resistor 84 connected to an operation amplifier 85 which produces a waveform output 86.

Figure 3:
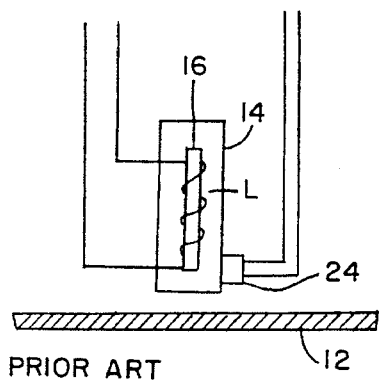
FIG. 3 shows the prior art eddy current probe over a chemical sensor film.

The probe may consist of an eddy current coil such as that shown in FIG. 3 or 6, or may be constructed from a ferrite core which has been wound using magnet wire. The chemically sensitive material may be placed between the magnet wire windings. The signal generator is capable of swept frequency operation and is preferably a direct digital signal generator. The resonant frequency can be measured using either an amplitude or phase detector.

Figure 10:
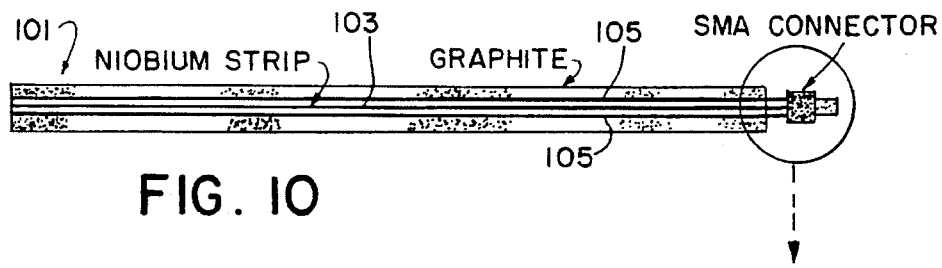
FIG. 10 shows a coplanar transmission line used as a high temperature chemical sensor.
Figure 11:
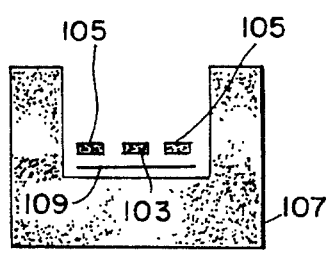
FIG. 11 shows an end view of the system shown in FIG. 10.
Figure 12:
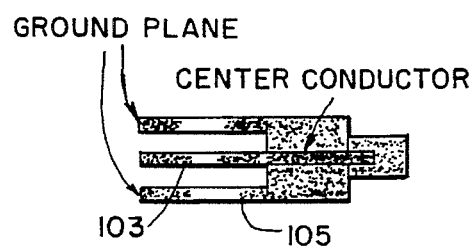
FIG. 12 is a detail of the ground planes and transmission line shown in FIG. 10.

FIGS. 10, 11 and 12 show a chemical sensor system 101 microstrip line coplanar line, coupled microstrip line or other microwave transmission line 103, with ground planes 105 within a graphite enclosure 107, are placed in the vicinity of a chemically alterable film 109.

In one configuration of the instrument, wound inductor coils are positioned below a removable chemical sensor film. The coils are excited separately through a multiplexer or in combination with one another through parallel excitation circuits. Detection of the coupled impedance, resonance frequency change or phase lag through each inductor provides a means of determining the response of sections of the film having different chemical responses to the analyte. The digital signal processor or system microprocessor used in the instrument can be used to perform a multivariate analysis to determine the analyte identity and concentration.

The advantages of eddy current, microwave and resonant chemical sensors include the following:

Noncontact operation of the eddy current probe allows rugged sensor design.

The sensor may be formed from noncontinuous films or films with high porosity for use in fouling applications.

The eddy current coupling can be designed so that the signal strength goes from zero to a large value over a small range of probe conductivity resulting in a large instrument response.

The combination of eddy current instrumentation and conductive polymer sensor design provides a sensitive and selective method of chemical analysis.

No reference electrode is required.

In the present invention, the instrument is applied to the measurement of chemical concentration through the use of a chemically-sensitive coating on the eddy current coil or in the vicinity of the eddy current coil which may produce a change in impedance of the probe through induced eddy currents in the coating.

The eddy current or resonance circuit chemical detector of the present invention is a non-contact means of measuring chemical species identity and concentration. The chemical detector is therefore resilient and does not require reference electrodes as do most electrochemical methods. The present chemical sensor can be extremely selective as a result of data available on the change in vector impedance of the probe, the change in resonant frequency of the tuned circuit, and the availability of data to construct a vector response from multiple probes having differing chemistries. The probe can be used in circumstances where the temperature of the process is extreme.

While the invention has been described with reference to specific embodiments, modifications and variations of the invention may be constructed without departing from the scope of the invention, which is defined in the following claims.

We claim:

1. a chemical sensing apparatus for measuring analytes comprising:

an eddy current probe;

an electromagnetic transducer connected to the probe;

a chemically sensitive material on or adjacent said eddy current probe;

means connected to said probe for inducing current in said material; and detector means for detecting a change in impedance or resonant frequency of the probe through induced eddy currents in the material indicative of the analyte to be sensed.

2. A chemical sensing apparatus for measuring analytes comprising:

a resistance inductance capacitance probe;

an electromagnetic transducer connected to the probe;

a chemically sensitive material on or adjacent said eddy current probe;

means connected to said probe for inducing current in said material; and detector means for detecting a change in impedance or resonant frequency of the probe through induced eddy currents in the material indicative of the analyte to be sensed.

3. The apparatus of claim 2, wherein the probe is a microwave or millimeter wave circuit and the detecter is a sensor detecting change in circuit parameters of the microwave or millimeter wave circuit.

4. The chemical sensor of claim 3, wherein the chemically sensitive material is a conducting polymer containing one or more dopants for providing sensitivity to a chemical of interest.

5. Chemical sensor apparatus for measuring chemical analytes comprising:

an electrically conductive or magnetically permeable material;

a contact area for contacting a chemical analyte with the material which changes the electrical conductivity or magnetic permeability of the material;

a probe having a circuit adjacent the material;

an excitation frequency source connected to the probe;

a sensor circuit connected to the probe for sensing change in circuit parameters of the probe, the sensor circuit further comprising a second frequency source; and a signal processor connected to the sensor circuit and an output connected to the processor for indicating the change in electrical conductivity or magnetic permeability of the chemical analyte sensed.

6. The apparatus of claim 5, wherein the excitation frequency source is a direct digital synthesizer.

7. The apparatus of claim 6, further comprising a first digital-to-analog converter connected between the synthesizer and the probe.

8. The apparatus of claim 7, further comprising an analog-to-digital converter connected between the probe and the second frequency source, and wherein the processor is a digital signal processor.

9. The apparatus of claim 7, further comprising a second digital-to-analog converter connected to the second frequency source, a mixer connected to the probe and to the second converter, and an analog-to-digital converter connected between the mixer and processor, and wherein the processor is a digital signal processor.

10. The apparatus of claim 9, further comprising a first upconverter positioned between the first digital-to-analog converter and the probe, and a second upconverter positioned between the second digital-to-analog converter and the mixer.

11. A chemical sensor apparatus for chemical analytes comprising:

a film of electrically conductive material for undergoing a change in conductivity or magnetic permeability when contacted by a chemical analyte;

a circuit;

a probe positioned adjacent the film;

an electrical conductor in the probe connected to the circuit and being in electrical isolation from the film;

a source of frequency connected to the circuit; and a sensor connected to the circuit for detecting changes in circuit parameters according to a chemical analyte on the film.

12. The apparatus of claim 11, wherein the probe is an eddy current probe and wherein the conductor is an electromagnetic coil.

13. The apparatus of claim 12, wherein the film is a conductive coating containing a chemically active material.

14. An eddy current chemical sensor for sensing a chemical analyte comprising an eddy current measuring probe having an electromagnetic coil and a conductive coating containing a chemically sensitive alterable material near the coil, and an eddy current measuring system connected to the coil for directly measuring complex impedance of a circuit connected to the coil indicative of the analyte to be sensed.

15. An electromagnetic chemical sensor for sensing a chemical analyte comprising a chemically sensitive alterable film, an adjustable tuned resistance, inductance, capacitance circuit, and a second circuit connected to the adjustable tuned resistance, inductance, capacitance circuit and containing one or more direct digital synthesizer circuits and one or more digital signal processor circuits in proximity to the chemically sensitive alterable film.

16. The chemical sensor of claim 15, wherein the chemically sensitive film is a conducting polymer containing one or more dopants for providing sensitivity to a chemical of interest.

17. The chemical sensor of claim 15, wherein the chemically sensitive film is a rare earth perovskite oxide.

18. The electromagnetic chemical sensor of claim 15 further comprising a microstrip line, coplanar line, coupled microstrip line or other microwave circuit transmission line placed in the vicinity of the chemically alterable sensitive film.

19. The chemical sensor of claim 18, further comprising ground planes positioned proximate to the transmission line and the chemically alterable sensitive film, and wherein the chemically alterable sensitive film is a conducting polymer containing one or more dopants for providing sensitivity to a chemical of interest.

20. The chemical sensor of claim 19, further comprising an enclosure for containing the transmission line, the grounds and the sensitive film.

\* \* \* \* \*